United States Patent

Tuckey

[11] Patent Number: 6,063,064
[45] Date of Patent: May 16, 2000

[54] INCONTINENCE APPLIANCE

[76] Inventor: Donald L. Tuckey, 9870 Maple Rd., Frankenmuth, Mich. 48734

[21] Appl. No.: 09/067,876

[22] Filed: Apr. 28, 1998

Related U.S. Application Data

[60] Provisional application No. 60/046,834, May 5, 1997.

[51] Int. Cl.[7] .................................................. A61F 5/44
[52] U.S. Cl. ........................................ 604/385.1; 604/387
[58] Field of Search ............................... 604/385.1, 387, 604/385

[56] References Cited

U.S. PATENT DOCUMENTS

| | | |
|---|---|---|
| D. 242,655 | 12/1976 | Cade et al. . |
| D. 243,883 | 3/1977 | Cade et al. . |
| 1,263,797 | 4/1918 | Norquist . |
| 2,031,638 | 2/1936 | Emery, Jr. . |
| 3,570,489 | 3/1971 | Brown . |
| 3,690,321 | 9/1972 | Hirschman . |
| 3,905,372 | 9/1975 | Denkinger . |
| 4,595,391 | 6/1986 | Johnson et al. . |
| 4,846,818 | 7/1989 | Keldahl et al. . |
| 5,074,855 | 12/1991 | Rosenbluth et al. . |
| 5,295,984 | 3/1994 | Contene et al. . |
| 5,336,208 | 8/1994 | Rosenbluth et al. . |
| 5,484,429 | 1/1996 | Vukos et al. . |

*Primary Examiner*—John G. Weiss
*Assistant Examiner*—Kelvin Hart
*Attorney, Agent, or Firm*—Reising, Ethington Barnes, Kisselle, Learman & McCulloch, P.C.

[57] ABSTRACT

A urinary incontinence appliance constructed according to the invention includes hydrophilic absorbing media encased in a water-impermeable sheath having a closed end that is inserted into the vagina of the user and an open end external to the vagina that is form fit to cover the urethra of the user. The external open end portion acts to funnel any urine that may escape from the urethra into the interior of the sheath where it is captured and wicked by the absorbent media within the vagina.

7 Claims, 4 Drawing Sheets

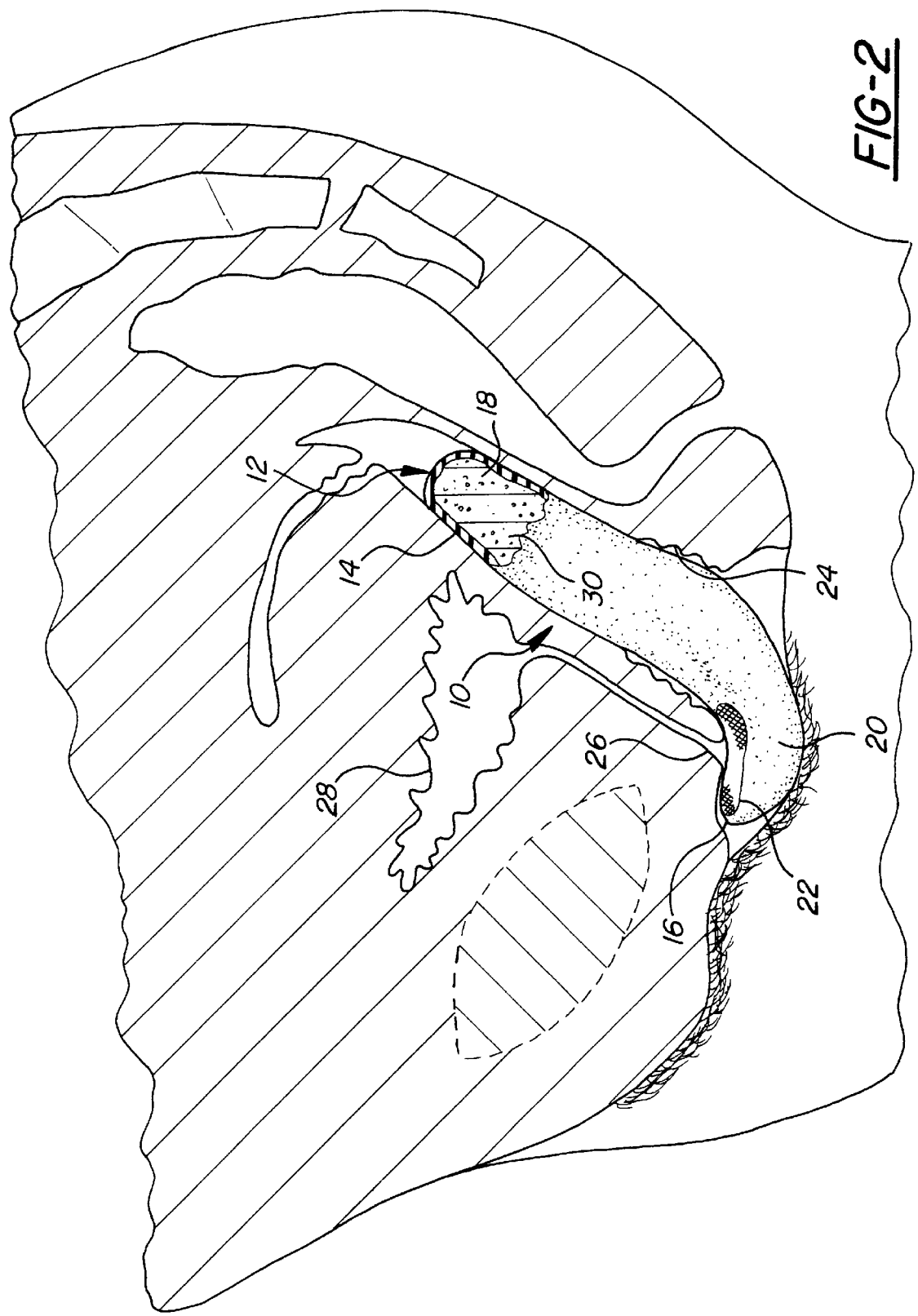

INCONTINENCE APPLIANCE

This Appln claims benefit of Provisional Appln No. 60/046,834 May 5, 1997.

This invention relates to female urinary incontinence appliances.

BACKGROUND OF THE INVENTION

Many women suffer from a condition known as urinary incontinence, resulting in partial or complete loss of bladder control. The typical non-surgical approach to managing this condition has been for such women to wear an external pad which absorbs and retains any urine lost from the bladder. Depending on the severity of the condition, a small pad or complete absorbent undergarment may be required to accommodate the urine loss.

Although such external absorbent perineal pads are effective at capturing lost urine and are simple to use, they have inherent disadvantages which many women find objectionable. Such pads tend to be bulky and for some uncomfortable to wear, especially when wet. Prolonged contact with such pads can irritate the delicate skin tissues in contact with the pad, causing chaffing, soreness, and general discomfort. Some individuals may develop skin allergies as a result of prolong use of such pads. In severe cases the user may no longer be able to wear such external pads. Other complaints often expressed about external absorbent pads is that they are unable to contain the odor of urine when wet.

The present invention overcomes or greatly minimizes all of the foregoing objections.

SUMMARY OF INVENTION

A urinary incontinence appliance constructed according to the invention includes hydrophilic absorbing media encased in a water-impermeable sheath having a closed end that is inserted into the vagina of the user and an open end external to the vagina that is form fit to cover the urethra of the user. The external open end portion acts to funnel any urine that may escape from the urethra into the interior of the sheath where it is captured and wicked by the absorbent media within the vagina.

The appliance may be a disposable device such that when the absorbent capacity of the media has been reached or when the vaginal bulk becomes uncomfortable to the wearer, she may simply replace the appliance with a fresh one.

One of the principal advantages of the invention is that the absorbent media which absorbs and holds the urine is internal to the vagina and encased in a water-impermeable sheath. The internal disposition and encasement of the media eliminates external bulk normally associated with the traditional external pads and absorbent undergarments as well as the urine odor associated with the use of such external pads and garments.

The invention has the further advantage of minimizing the amount of tissue exposed to a wet pad, since all but a small portion of the absorbent media at the opening of the sheath is accommodated within the vagina and encased by the water-impermeable sheath to shield the vaginal wall tissues of the wearer from contact with the absorbent media. The invention contemplates that such a minimal contact incontinence device may be utilized even by those patients who have allergies to traditional external pads and, importantly, may be utilized in the first instance by those susceptible to such skin allergies to prevent or at least minimize the occurrence of such allergies.

The invention contemplates various embodiments of the basic intravaginal incontinence appliance having features which aid in retaining the closed intravaginal portion of the appliance within the vagina. According to a particular embodiment, the closed end of the sheath may be somewhat flared such that as the absorbent media within the sheath absorbs urine and expands, the closed end of the appliance accommodated within the vagina expands disproportionately to that of the open end to effectively wedge the device within the vagina so that it is self-supporting against removal. A further advantage with this feature is that as the media collects more urine, its self-retaining wedging effect increases counteracting the force of the additional weight tending to withdraw the device from the vagina. Still yet another advantage is that the internal bulk of the absorbent media provides support to the bladder and urethra tube which, in some case, may serve to lessen the severity of the users incontinence where such condition is attributable to the loss of muscle or tissue support in those regions.

According to another particular feature, the closed intravaginal sheath may be fitted with a retaining device that, when the sheath is inserted in the vagina, expands to support and retain the appliance in place. The retainer may take the form of a pair of spaced arms internal to the sheath and extending toward its closed end and joined adjacent the closed end by an elastic member which applies a constant outward biasing force to the forks causing them to take on a divergent wedge-shaped form when extended into the vagina.

Other means for retaining the appliance in place may include a belt or strap worn about the hips of the user and connected to the appliance to effectively suspend the appliance in place. Another means contemplated for supplementing the support of the appliance is to wear it in combination with a thin pad which serves to apply and maintain upward pressure on the appliance to hold it in place.

Those skilled in the gynecological field will appreciate that the retaining system for the basic intravaginal device may take on these and various other forms and will depend a great deal on the needs of a particular wearer. For those individuals who have good intravaginal muscle support, the self-retaining construction may be all that is needed. Others with weakened muscle support may require the use of the supplemental retaining devices such as the flared sheath design, flared spring arms, the belt, or external pad to name a few.

THE DRAWINGS

A presently preferred embodiment of the invention is disclosed in the following description and in the accompanying drawings, wherein:

FIG. 2 is a longitudinal cross-sectional view of the appliance of FIG. 1 shown installed in place within the vagina of a user;

DETAILED DESCRIPTION

Figure 1:
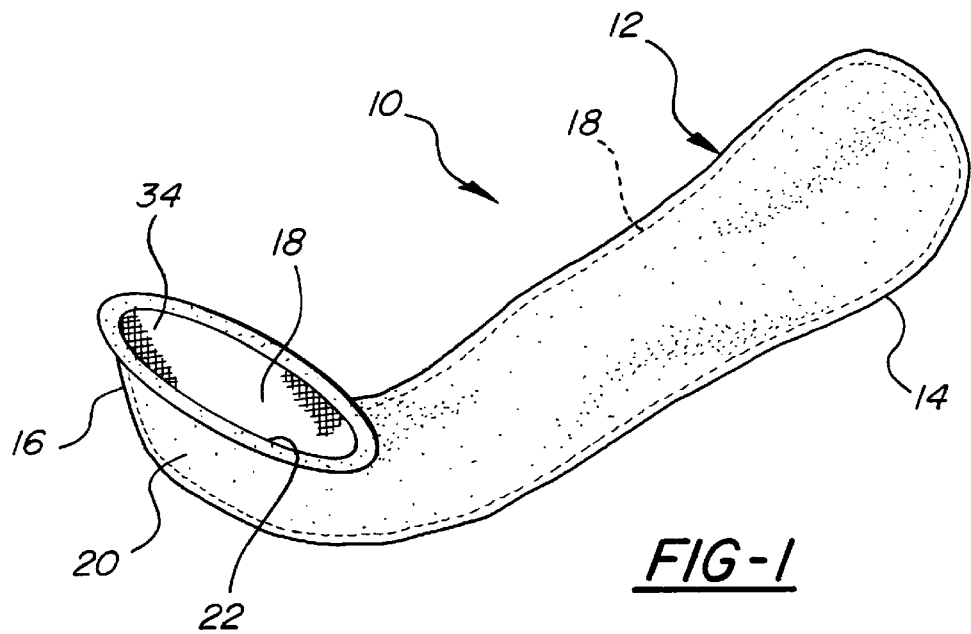
FIG. 1 is a perspective view of an incontinence appliance constructed in accordance with a first presently preferred embodiment of the invention.

Turning now in more detail to the drawings, FIG. 1 illustrates a female incontinence appliance 10 constructed in accordance with a presently preferred embodiment of the invention. The appliance 10 comprises a generally elongate tubular sheath 12 having a closed end 14 and an open end 16. Accommodated within the sheath 12 is a hydrophilic absorbent medium 18, only a small portion of which is exposed at the open end 16 of the sheath 12. The sheath 12 is fabricated of a water-impermeable material, such as latex, silastic, or other neutral, hypoallergenic elastic materials. The closed end portion 14 of the sheath 12 is preferably a thin walled construction and may be constructed much like a condom. The front open end portion 16 may be fabricated of the same or different material and preferably of a pliable, yet form fitting construction such that it provides an upwardly extending cup-shaped shield 20 and an opening or rim 22.

Figure 3:
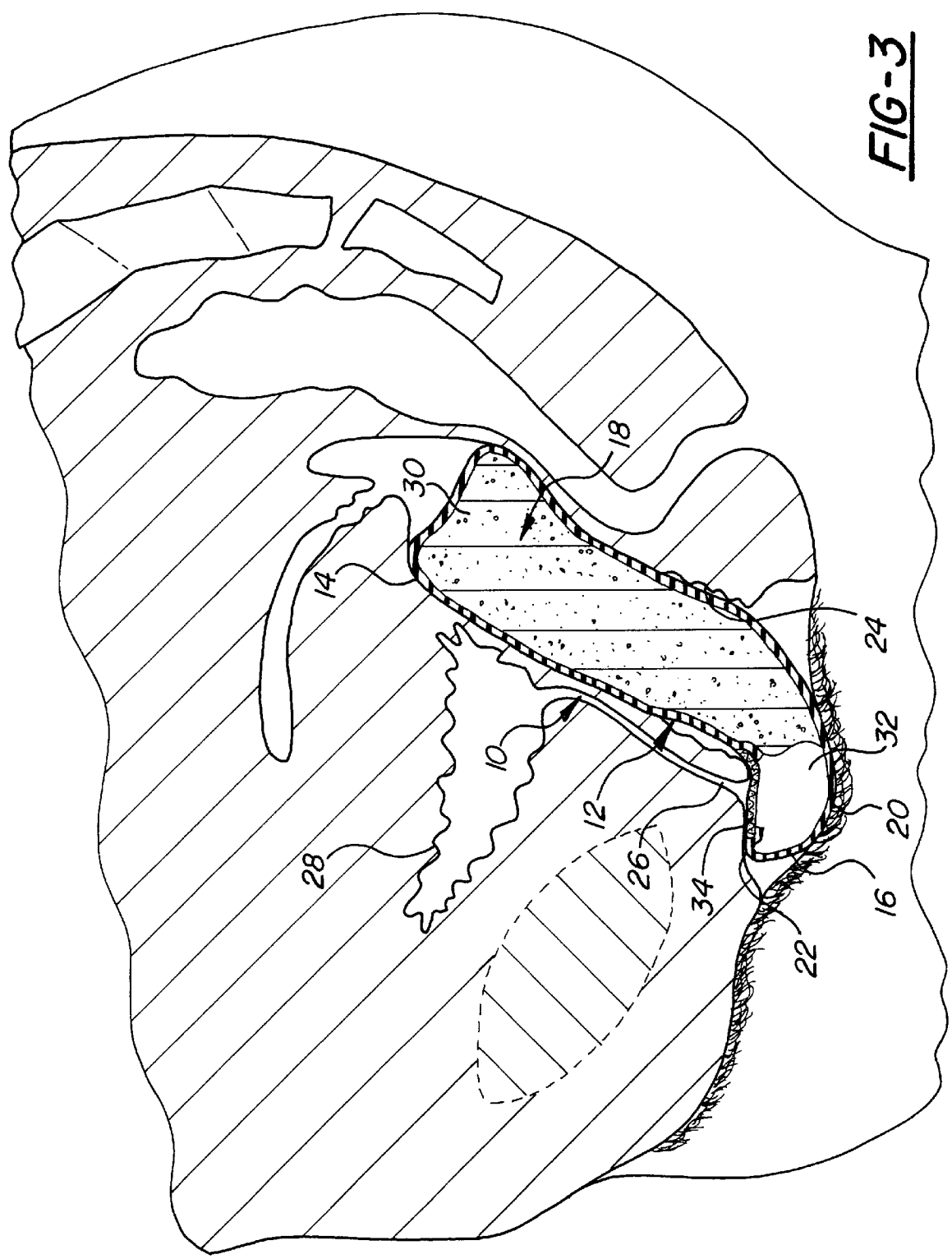
FIG. 3 is a view like FIG. 2 but with the absorbent media expanded from absorption of urine.

FIGS. 2 and 3 illustrate the appliance 10 in use. As shown, the closed end portion 14 is extended into the vaginal canal 24 of the user with the open end 16 remaining external such that the opening or rim 22 of the sheath 12 encompasses the urethral opening or meatus 26 of the wearer leading from the bladder 28. In this way, the absorbent medium 18 is primarily internal to the user and that which is external is sealed by the rim 22 of the sheath 12 about the urethra region 26.

Any urine that leaks from the bladder 28 is funneled into the interior of a sheath 12 through the opening 22. Such urine is wicked by the absorbent medium 18 and contained wholly within the sheath 12. The water-impermeable nature of the sheath 12 prevents fluids from being transmitted into or out of the sheath thereby retaining the urine and any odors associated therewith within the confines of the sheath 12.

FIG. 3 illustrates a preferred construction of the closed end region 14 which is caused to flare or enlarge disproportionally with the remainder of the appliance 10 as urine as absorbed. As illustrated, the sheath 12 is preferably constructed with a flared configuration at its closed end 14 such that as the urine is absorbed and wicked toward the closed end, the absorbent medium 18 in the vicinity expands and flares the closed end 14 to present a divergent wedge-shaped configuration to the appliance 10. Such shape helps retain the closed end 14 within the vagina 24, and the wedging effect is increased proportionally with the amount of urine absorbed. In this way, the appliance 10 increases its self-supporting properties as more urine is absorbed, counteracting the downward gravitational force acting on the appliance 10 as it becomes heavier with urine. By "wedge-shaped", it is meant to include any bulbous or enlarged configurations that serve to wedge or lodge the closed end 14 within the vagina 24.

The preferred absorbent media 18 provided within the sheath 12 is preferably of a super-absorbent material, such as the hydrophilic gelling beads commonly used in children's diapers and is capable of expanding to many times its size when absorbing urine. A wicking pad 32 and overlying dry cloth layer 34 may be provided at the opening 22 such that the portion of the medium 18 in contact with the users skin is kept dry and free of urine. The construction and materials for the pad 32 and dry layer 34 may be any of various forms commonly used in diaper applications, sanitary napkins, and the like.

Figure 4:
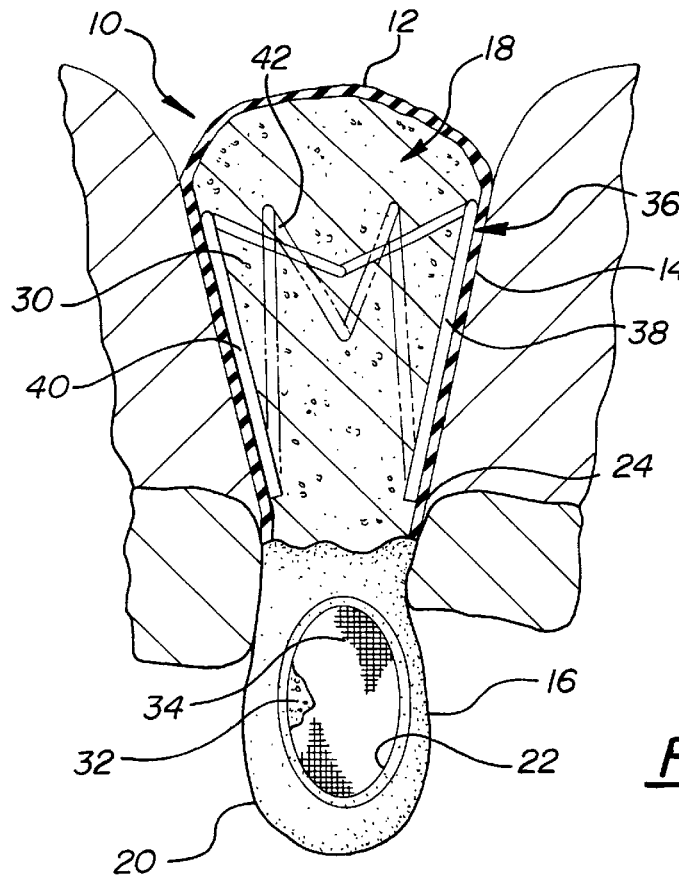
FIG. 4 is a top cross-sectional view showing a supplemental retaining system for the appliance.

FIG. 4 illustrates a supplemental retaining system 36 that may be used in conjunction with the application 10 described above. As shown, the system 36 comprises a pair of spaced arms 38, 40 accommodated within the sheath 12 and extending generally the length of the closed end portion 14. The arms 38, 40 are joined at their ends adjacent the closed end 14 of the sheath by an elastic spring member 42 which acts on the arms 38, 40 biasing them constantly apart so that they diverge outwardly from one another in the direction of the closed end 14 to provide a wedge shape to the intravaginal portion 14. The spring 42 may comprise a rubber or plastics piece or a protected metal piece which spans the arms and in its unloaded state spreads them apart, yet is elastically yieldable to enable the user to pinch the arms 38, 40 toward one another to accommodate the insertion of the sheath 12 into the vagina 24. Upon releasing the arms, the spring 42 returns the arms to their divergent condition, thereby wedging the closed end portion 14 to the sheath 12 within the vagina 24.

Figure 5:
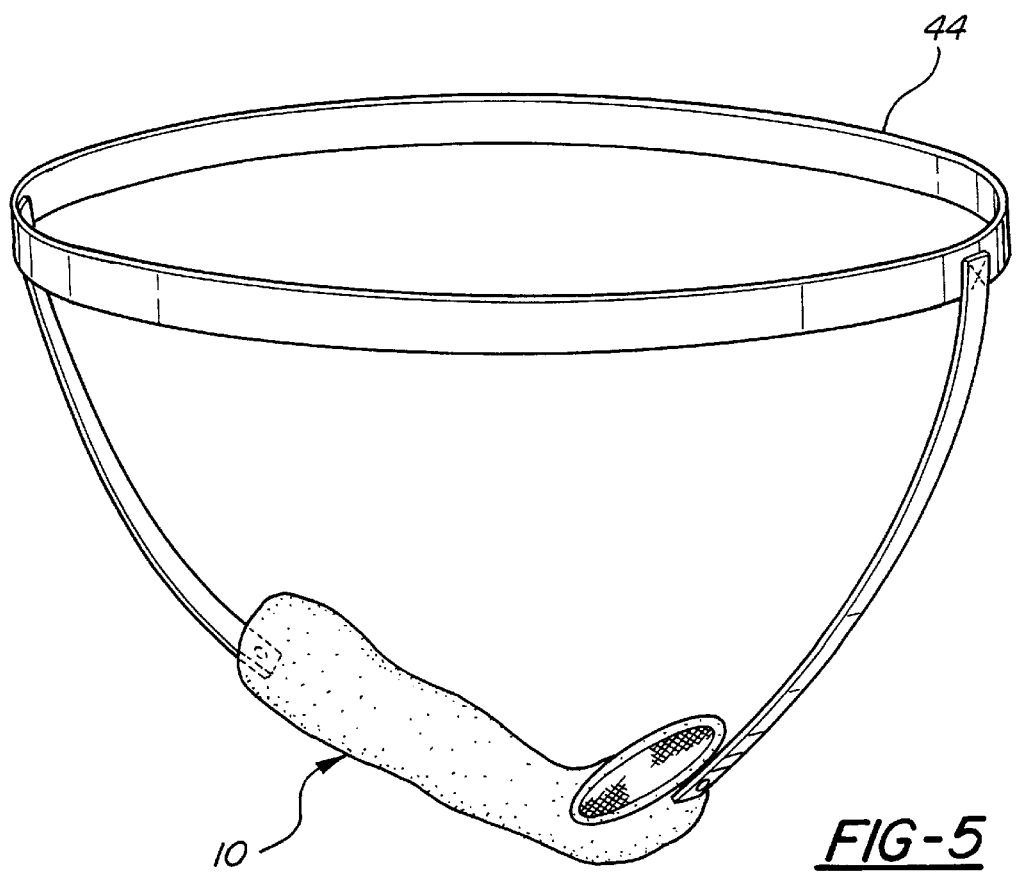
FIG. 5 is another embodiment of a supplemental retaining system of the invention.

FIG. 5 illustrates another means of retaining the appliance 10 within the vagina 24, and in this case is in the form of a belt or strap system 44 that may arranged about the waist or hips of the wearer to effectively suspend the appliance 10 in place. It is preferred that the appliance 10 be separable from the belt system 44 such that the same belt 44 may be used with different appliances 10.

Figure 6:
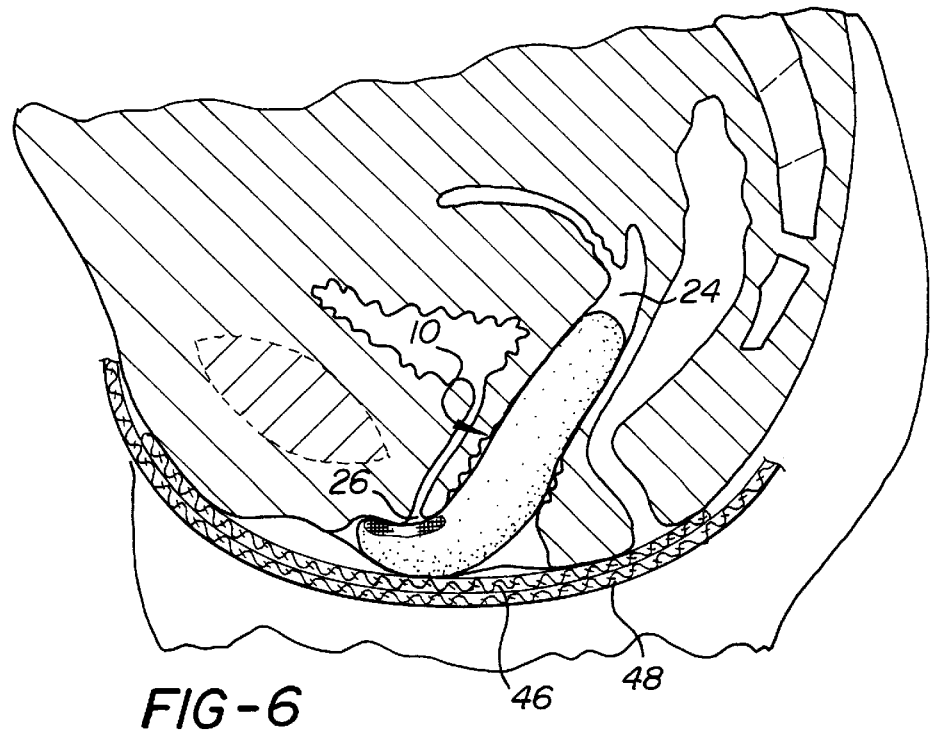
FIG. 6 is still a further embodiment of a supplemental retaining system of the invention.

FIG. 6 illustrates yet another retaining system that may be used in conjunction with the appliance 10. In this embodiment, the appliance 10 is installed and used in the same manner as described above except that a thin supplemental external pad 46 is worn between the appliance 10 and the undergarment 48 in order to apply upward pressure on the underside of the shield 20 to help hold the closed end portion 14 within the vagina 24. The pad 46 is preferably a thin panty liner type pad like any of a number of types presently in use. The invention contemplates that the pad 24 could be constructed as an integral part of the appliance 10 to provide an all-in-one unit with the pad 46 serving as a support device for the shield 12 and if desired as a secondary absorbent device in the unlikely event that urine were to escape pass the rim 22 of the sheath 12.

The disclosed embodiments are representative of presently preferred forms of the invention, but are intended to be illustrative rather than definitive thereof. The invention is defined in the claims.

I claim:

1. An intra-vaginal urinary incontinence device comprising:

hydrophilic absorbent medium; and an elongate sheath fabricated of pliable, water-impermeable material encasing said absorbent medium, said sheath having an elongate main body portion closed at one end thereof and extendible into the vagina of a user so as to locate said medium within the vagina and a contoured open end portion positionable external to the vagina and configured to overly the urethra region of the user while said main body portion is disposed within the vagina, said open end being operative to funnel any urine that may escape from the urethra of the user into said sheath where the urine is absorbed by said medium and thereby contained within said sheath interiorly of the vagina, said medium being expandable in response to absorbing urine, and said sheath material being elastic and expandable with said medium.

2. The device of claim 1 wherein said closed end of said device is expandable disproportionately greater than that of said open end region to provide a wedging action within the vagina.

3. The device of claim 1 wherein said device is generally J-shaped.

4. The device of claim 1 wherein said open end of said sheath is turned generally toward said closed end presenting a frontal shield and an annular rim defining an opening into the interior of said sheath in communication with said medium.

5. The device of claim 1 wherein said device includes self retaining means for supporting said closed end portion of said device within the vagina of the user.

6. The device of claim 5 wherein said self-retaining means comprises a laterally expandable retainer disposed within said sheath adjacent said closed end thereof operative to act on the walls of the vagina to restrain the closed end portion of said sheath against removal from the vagina of the user once installed.

7. An intra-vaginal urinary incontinence device comprising: a generally elongate tubular sheath fabricated of a pliable, elastic, water-impermeable material having a closed end and a contoured open end, said open end being turned generally toward said closed end presenting a frontal shield and an annular rim defining an opening into the interior of said sheath; and a hydrophilic expandable medium disposed within and encased by said sheath so as to be shielded from exposure except for at said open end of said sheath, said closed end being insertable into the vagina of a user so as to dispose a majority of said medium within the vagina and said contour of said open end being such that said rim is simultaneously positionable over the urethra region of the user causing any urine that may escape the urethra to be funneled into the sheath through said open end thereof and be absorbed by said medium and thereby contained within said sheath while disposed within the vagina of the user, said medium being expandable in response to absorbing the urine and said elastic sheath being expandable with said medium.

* * * * *

UNITED STATES PATENT AND TRADEMARK OFFICE
CERTIFICATE OF CORRECTION

PATENT NO. : 6,063,064
DATED : May 16, 2000
INVENTOR(S) : Donald L. Tuckey

It is certified that error appears in the above-indentified patent and that said Letters Patent is hereby corrected as shown below:

Title page, item [56] under References Cited, add --
    Patent No. 2,613,670 - Sokolik --.
Change "Patent No. 4,595,391" to -- Patent No. 4,595,392 --.

Signed and Sealed this

Twentieth Day of March, 2001

Attest:

NICHOLAS P. GODICI

*Attesting Officer*     Acting Director of the United States Patent and Trademark Office